United States Patent [19]
Place

[11] Patent Number: 5,482,039
[45] Date of Patent: Jan. 9, 1996

[54] PROCESS FOR DIAGNOSING ERECTILE DYSFUNCTION, AND RELATED METHODS OF TREATMENT

[75] Inventor: Virgil A. Place, Kawaihae, Hi.

[73] Assignee: Vivus, Inc., Menlo Park, Calif.

[21] Appl. No.: 218,453

[22] Filed: Mar. 25, 1994

[51] Int. Cl.[6] .......................... A61B 5/055; A61B 8/00; A61M 31/00

[52] U.S. Cl. ................... 128/653.1; 128/653.2; 128/660.01; 128/774; 604/19; 604/54; 604/57; 604/93; 604/181; 604/288

[58] Field of Search ............................ 128/653.1, 653.2, 128/660.01, 774; 601/2; 600/29, 30, 38; 604/20, 19, 48, 54, 57, 93, 181, 288

[56] References Cited

U.S. PATENT DOCUMENTS

| | | |
|---|---|---|
| 3,826,828 | 7/1974 | Morel . |
| 4,127,118 | 11/1978 | Latorre . |
| 4,311,707 | 1/1982 | Birnbaum et al. . |
| 4,334,543 | 6/1982 | Fehr . |
| 4,485,821 | 12/1984 | Iinuma . |
| 4,612,937 | 9/1986 | Miller . |
| 4,801,587 | 1/1989 | Voss et al. . |
| 4,829,991 | 5/1989 | Boeck ............................. 600/39 |
| 4,840,952 | 6/1989 | Gamble et al. ................ 514/253 |
| 4,928,706 | 5/1990 | Trick ............................. 128/774 |
| 5,059,603 | 10/1991 | Rubin ............................. 514/264 |
| 5,145,852 | 9/1992 | Virag ............................. 514/307 |
| 5,219,885 | 6/1993 | Frölich et al. . |
| 5,236,904 | 8/1993 | Gerstenberg et al. ............ 514/12 |
| 5,242,391 | 9/1993 | Place et al. ..................... 604/54 |
| 5,270,323 | 12/1993 | Milne, Jr. et al. ............. 514/309 |
| 5,333,621 | 8/1994 | Denzer ............................. 600/38 |
| 5,336,678 | 8/1994 | Cavallini ......................... 514/275 |

FOREIGN PATENT DOCUMENTS

| | | | |
|---|---|---|---|
| 1111759 | 9/1984 | U.S.S.R. ........................ 601/2 |
| WO90/02545 | 3/1990 | WIPO . |
| WO91/16021 | 10/1991 | WIPO . |

OTHER PUBLICATIONS

Krane et al., "Medical Progress: Impotence," *The New England Journal of Medicine* 321(24):1628–1639 (1989).

T. I–Sheng Hwang et al., "Impotence Evaluated by the Use of Prostaglandin E1," *The Journal of Urology* 141:1357–1359 (1989).

Steif et al, "Mid–term results of autoinjection therapy for erectile dysfunction," *Urology* 31(6):483–485 (1988).

R. Virag et al., "Intracavernous Injection of Papaverine as a Diagnostic and Therapeutic Method in Erectile Failure," *Angiology—Journal of Vascular Diseases*, Feb. 1984, pp. 79–87.

*Primary Examiner*—Krista M. Zele
*Attorney, Agent, or Firm*—Reed & Robins

[57] ABSTRACT

A method for diagnosing vasculogenic erectile dysfunction, including vasculogenic impotence and Peyronie's syndrome, is provided. The method involves transurethral administration of a vasodilating agent to induce an erection, followed by hemodynamic evaluation using duplex ultrasonography, NMR, angiography, or the like. Kits for conducting the diagnostic method are provided as well, as are methods of treatment based on the diagnostic conclusion.

51 Claims, 4 Drawing Sheets

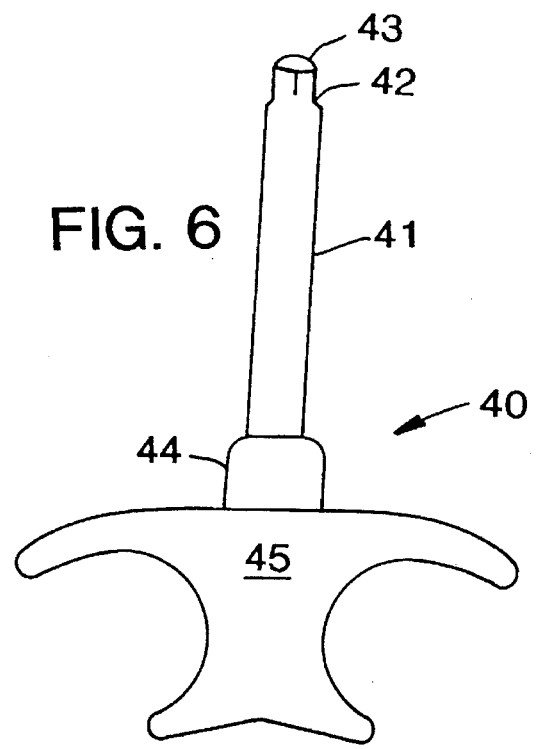
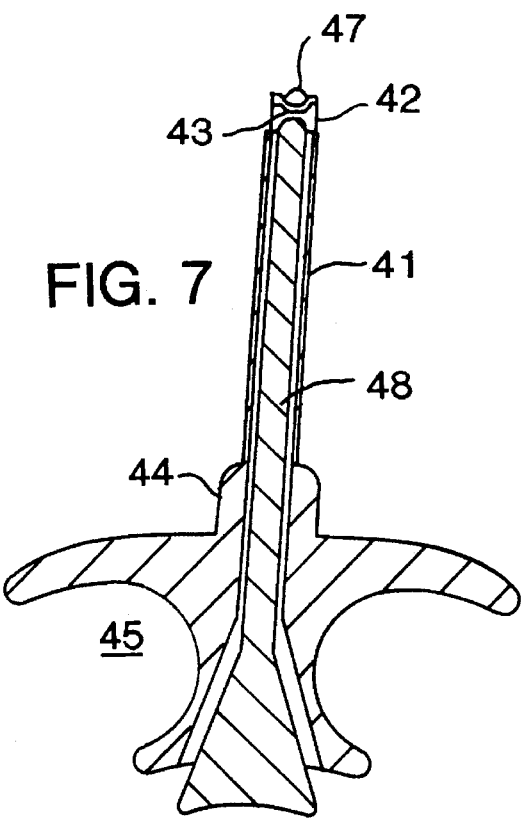
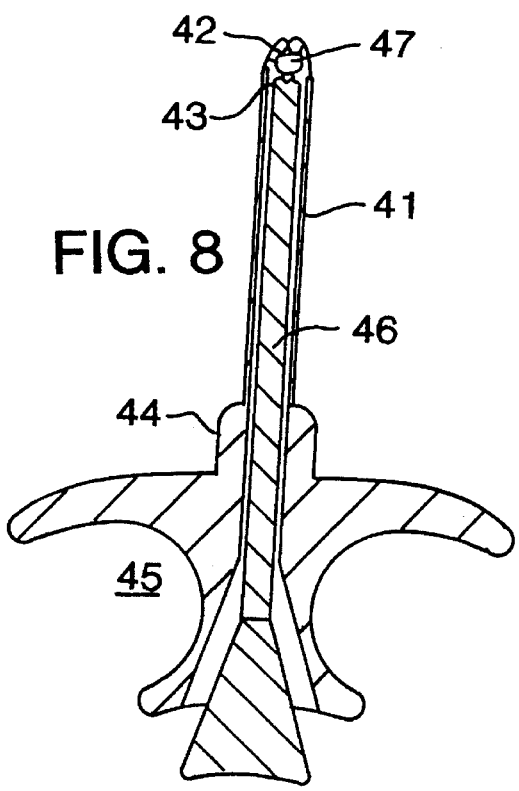

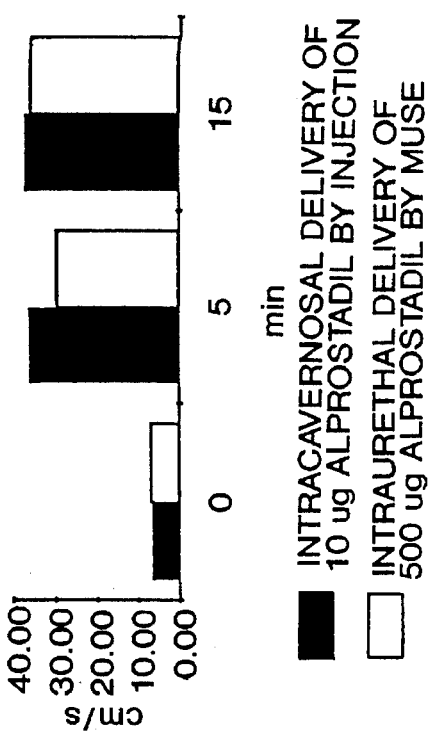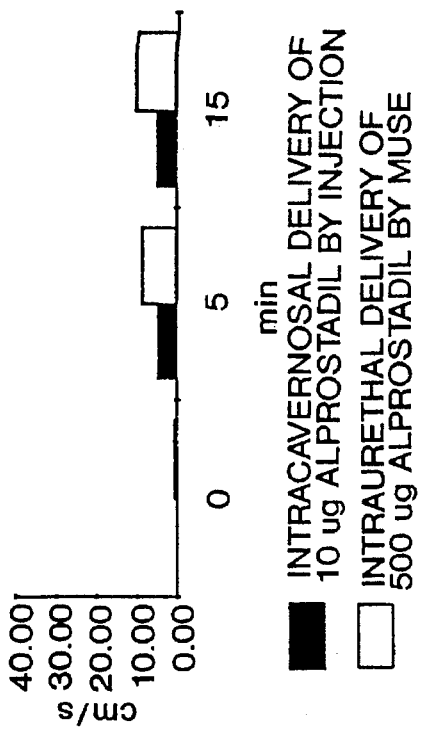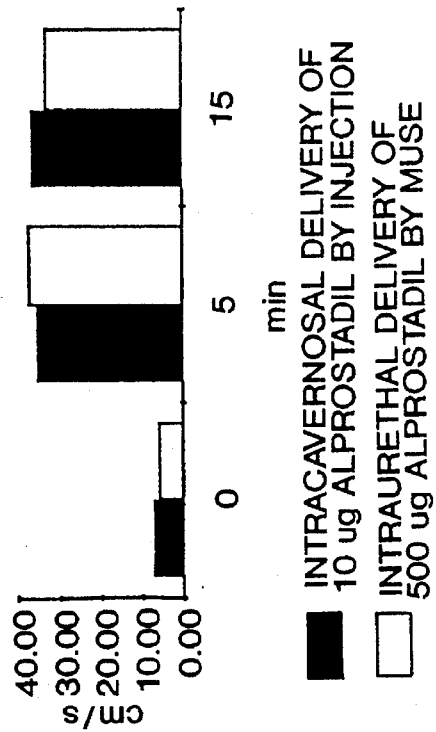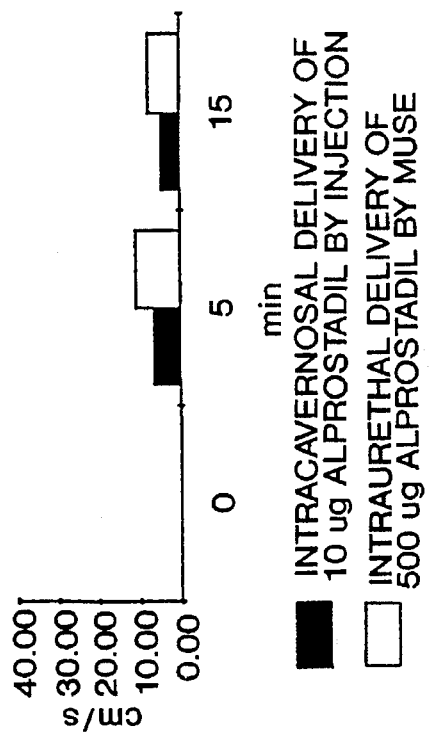

PROCESS FOR DIAGNOSING ERECTILE DYSFUNCTION, AND RELATED METHODS OF TREATMENT

TECHNICAL FIELD

This invention relates generally to the diagnosis of erectile dysfunction. More particularly, the invention relates to a novel noninvasive procedure for diagnosing erectile dysfunction, particularly vasculogenic erectile dysfunction, by measuring various penile hemodynamic parameters subsequent to transurethral administration of a selected vasoactive agent. The invention additionally relates to kits for carrying out the diagnostic method, and to methods of treatment deriving from the diagnosis.

BACKGROUND

Impotence is the consistent inability to achieve or sustain an erection of sufficient rigidity for sexual intercourse. It has recently been estimated that approximately 10 million American men are impotent (R. Shabsigh et al., "Evaluation of Erectile Impotence," *Urology* 32:83–90 (1988); W. L. Furlow, "Prevalence of Impotence in the United States," *Med. Aspects Hum. Sex.* 19:13-6 (1985)). Impotence is recognized to be an age-dependent disorder, with an incidence of 1.9 percent at 40 years of age and 25 percent at 65 years of age (A. C. Kinsey et al., "Age and Sexual Outlet," in *Sexual Behavior in the Human Male*, A. C. Kinsey et al., eds., Philadelphia, Pa,: W. B. Saunders, 218–262 (1948)). In 1985 in the United States, impotence accounted for more than several hundred thousand outpatient visits to physicians (National Center for Health Statistics, National Hospital Discharge Survey, 1985, Bethesda, Md., Department of Health and Human Services, 1989 DHHS publication no. 87-1751). Depending on the nature and cause of the problem, treatments include psychosexual therapy, hormonal therapy, administration of vasodilators such as nitroglycerin and α-adrenergic blocking agents ("α-blockers"), oral administration of other pharmaceutical agents, vascular surgery, implanted penile prostheses, vacuum constriction devices and external aids such as penile splints to support the penis or penile constricting rings to alter the flow of blood through the penis.

A number of causes of impotence have been identified, including vasculogenic, neurogenic, endocrinologic and psychogenic. Impotence can also be a side effect of various classes of therapeutic drugs, or can be associated with various diseases, including diabetes, multiple sclerosis and sickle cell anemia. Impotence resulting from any one of these causes can be exacerbated by additional factors such as cigarette smoking, a poor diet, or the like.

Vasculogenic impotence occurs either as a result of arterial occlusion—the obstruction of adequate blood flow to the penile arteries necessary for erection— or as a result of cavernovenous leakage, i.e., excess venal outflow. As explained by Krane et al., "Medical Progress: Impotence," *The New England Journal of Medicine* 321(24):1628–1639 (1989), alteration in the flow of blood to and from the penis is believed to be the most frequent organic cause of impotence.

Current methods of diagnosing vasculogenic impotence or other vasculogenic erectile disorders involve measurement of penile hemodynamics after inducing an erection by direct injection of a vasoactive agent into the corporal cavernosum. For example, T. I-Sheng Hwang et al., "Impotence Evaluated by the Use of Prostaglandin E1," *The Journal of Urology* 141:1357–1359 (1989), describes a method for diagnosing impotence using intracavernous injection of prostaglandin E1, followed by subcutaneous injection of $^{133}$xenon to enable hemodynamic evaluation of penile vascularity. Reference may also be had to R. Virag et al., "Intracavernous Injection of Papaverine as a Diagnostic and Therapeutic Method in Erectile Failure," *Angiology—Journal of Vascular Diseases*, February 1984, pp. 79–87, who describe a method for diagnosing erectile failure involving intracavernous injection of papaverine and measurement of subsequent arterial changes using Doppler ultrasound.

Such diagnostic techniques, involving injection of vasoactive agents using a hypodermic needle, are painful and frequently unacceptable to patients. In addition, intracorporeal injections have been associated with priapism, development of fibrosis at the injection site and hematomas.

There is accordingly a need in the art for a noninvasive method of diagnosing erectile dysfunction, particularly vasculogenic erectile dysfunction. As used herein, the term "vasculogenic erectile dysfunction" is used to refer not only to vasculogenic impotence, but also to Peyronie's syndrome, a condition characterized by fibrosis of the cavernous tissue and associated painful and distorted penile erection. The term is also used to refer to erectile dysfunction resulting from local vascularized injury or vasculogenic changes.

Accordingly, the method of the invention is useful to diagnose vasculogenic erectile dysfunction, i.e., to determine whether or not a patient's impotence is due to vasculogenic causes. Unlike the diagnostic methods of the prior art, the present technique is noninvasive, fast, cost-effective, and easy to perform.

SUMMARY OF THE INVENTION

Accordingly, it is a primary object of the present invention to address the aforementioned need in the art, by providing a novel technique for diagnosing erectile dysfunction, i.e., for determining whether or not a patient's erectile dysfunction is due to vasculogenic causes.

It is another object of the invention to provide a method for diagnosing vasculogenic erectile dysfunction which involves transurethral administration of a vasodilating agent followed by measurement of penile hemodynamics.

It is still another object of the invention to provide such a method wherein the measurement of penile hemodynamics is conducted using ultrasound or nuclear magnetic resonance ("NMR") spectroscopy.

It is yet another object of the invention to provide such a method wherein the vasculogenic erectile dysfunction is impotence or Peyronie's syndrome.

It is a further object of the invention to provide such a method wherein the hemodynamic parameters which are measured include cavernosal artery peak systolic velocity, cavernosal artery end diastolic velocity, maximum arterial dilation, and pressure.

It is still a further object of the invention to provide such a method wherein the vasodilating agent is a nitrate (e.g., nitroglycerin, isosorbide dinitrate, or nitric oxide compounds), a short-acting α-blocker, an ergot alkaloid, or a prostaglandin.

Additional objects, advantages and novel features of the invention will be set forth in part in the description which follows, and in part will become apparent to those skilled in the art upon examination of the following, or may be learned by practice of the invention.

In one aspect of the invention, a vasodilating agent is administered transurethrally to the patient undergoing evaluation, in an amount sufficient to induce erection of the penis and to maintain the erection for a time period sufficient to allow measurement of the hemodynamic parameters of interest. After erection has been induced, hemodynamic parameters such as cavernosal artery peak systolic velocity (PSV) cavernosal artery end diastolic velocity (EDV), and maximum arterial dilation are evaluated, preferably using duplex ultrasonography, although other techniques may be used as well. Pressure may also be measured, using a simple cuffing technique or a corpus cavernosagram. Based on the results of the hemodynamic evaluation, a determination is made as to whether there is penile vascular insufficiency; this will generally be the case when the measured PSV, EDV, maximum arterial dilation and/or pressure are below certain predetermined values.

In another aspect of the invention, a method is provided for treating erectile dysfunction. The method involves conducting the aforementioned diagnostic procedure, determining whether the patient's erectile dysfunction is due to vasculogenic causes, and treating the patient in a manner that comports with the diagnosis.

In a further aspect of the invention, a kit is provided for conducting the diagnostic method. Generally, the kit will include at minimum the drug to be administered, a device for administering the drug transurethrally, a sealed container housing the drug and device prior to use, and written instructions for carrying out the diagnostic method. The kit may include a means for administering the drug at different doses, or it may include different drugs. Measurement instruments may be included in the kit as well.

BRIEF DESCRIPTION OF THE DRAWINGS

FIG. 6 is a side view of another inserter construction for introducing a drug into the urethra.

FIG. 7 is a cross-section through the inserter of FIG. 6 in the filling position.

FIG. 8 is a cross-section through the inserter of FIG. 6 in the loaded position.

FIGS. 10 through 13 are graphs illustrating a comparison of a diagnostic method using transurethral administration of a vasodilating agent with the diagnostic method of the prior art, wherein the vasodilating agent is administered by intracorporeal injection.

DETAILED DESCRIPTION OF THE INVENTION

Figure 1:
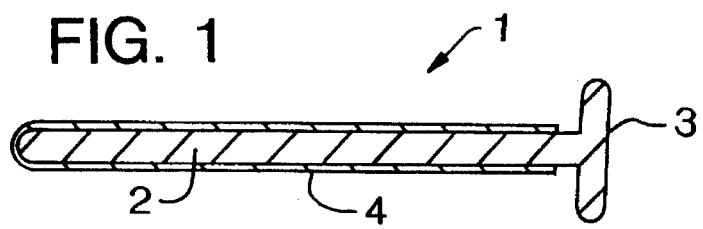
FIG. 1 is a cross-sectional view of one embodiment of a device which may be used in conjunction with the present invention, to administer a drug transurethrally.

Before describing the present invention in detail, it is to be understood that this invention is not limited to particular drugs, transurethral delivery systems or equipment for conducting penile hemodynamic measurements, as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "a vasodilating agent" or "vasodilator" includes a mixture of two or more such agents, reference to "a transurethral permeation enhancer" includes mixtures of two or more enhancers, and the like.

In describing and claiming the present invention, the following terminology will be used in accordance with the definitions set out below.

The terms "transurethral" or "intraurethral" as used to specify the mode of administration of vasodilator are used interchangeably to refer to delivery of the drug into the urethra such that drug contacts and passes through the wall of the urethra and enters into the bloodstream.

"Penetration enhancement" or "permeation enhancement" as used herein relates to an increase in the permeability of the skin or mucosal tissue to a selected pharmacologically active agent, i.e., so as to increase the rate at which the drug permeates through the skin and enters the bloodstream. "Transurethral permeation enhancers" increase the permeability of the urethral wall to drugs administered as described herein.

"Carriers" or "vehicles" as used herein refer to carrier materials suitable for transurethral drug administration, and include any such materials known in the art, e.g., any liquid, gel, solvent, liquid diluent, solubilizer, or the like, which is nontoxic and which does not interact with other components of the composition in a deleterious manner.

In order to carry out the method of the invention, a selected vasodilating agent is initially administered transurethrally to induce an erection. Suitable vasodilators include, but are not limited to: nitrates such as nitroglycerin and isosorbide dinitrate; long and short acting α-blockers such as phenoxybenzamine, dibenamine, doxazosin, terazosin, phentolamine, tolazoline, prazosin and trimazosin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; chlorpromazine; haloperidol; yohimbine; naturally occurring prostaglandins such as $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, and $PGF_{3\alpha}$; semisynthetic or synthetic derivatives of natural prostaglandins, including carboprost tromethamine, dinoprost tromethamine, dinoprostone, gemeprost, metenoprost, sulprostone and tiaprost; vasoactive intestinal peptides; and any other agent which is capable of producing an erection when administered transurethrally. For example, dopamine agonists such as apomorphine and bromocriptine, and opioid antagonists such as naltrexone have been reported to induce erection and they may also be useful in conjunction with this invention. See S.

Lal et al., "Apomorphine: Clinical Studies on Erectile Impotence and Yawning," *Prog. Neuropsychopharmacology* 13:329–339 (1989) and A. Fabbri et al., "Endorphins in Male Impotence, Evidence for Naltrexone Stimulation of Erectile Activity in Patient Therapy," *Psychoneuroendocrinology* 14(89):103–111.

Additionally, simultaneous administration of two or more vasodilating agents may be desirable and may in some cases exhibit a synergistic effect.

The vasodilator will typically be administered in a pharmaceutical composition containing one or more selected carriers or excipients, as noted above. Examples of suitable carriers for use herein include water, silicone, waxes, petroleum jelly, polyethylene glycol, propylene glycol, liposomes, sugars such as mannitol and lactose, and a variety of other materials. The composition may also include transurethral permeation enhancers, e.g., dimethylsulfoxide (DMSO), dimethyl formamide (DMF), N,N-dimethylacetamide (DMA), decylmethylsulfoxide ($C_{10}MSO$), polyethylene glycol monolaurate (PEGML), glycerol monolaurate, lecithin, the 1-substituted azacycloheptan-2-ones, particularly 1-n-dodecylcyclazacycloheptan- 2-one (available under the trademark Azone® from Nelson Research & Development Co., Irvine, Calif.), alcohols, or the like.

Figure 3:
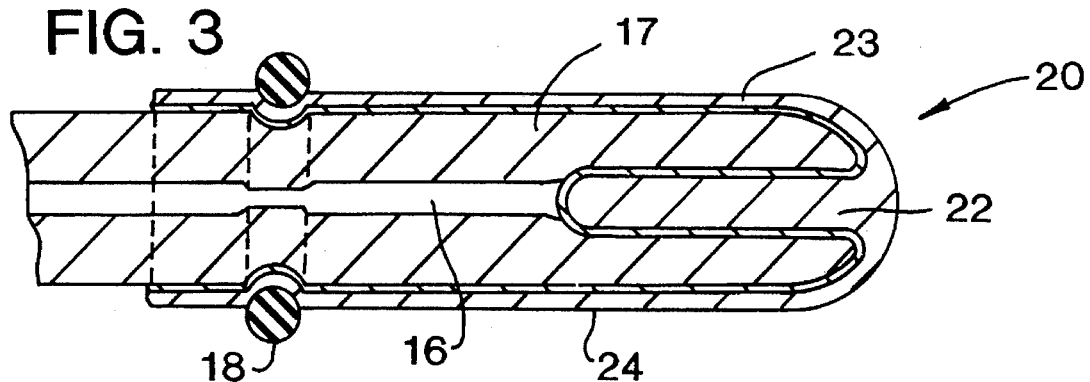
FIG. 3 is an exploded view of a penile insert which may be used in conjunction with the present invention.

The amount of vasodilating agent administered is selected such that it is sufficient to induce an erection. As explained in co-pending patent application Ser. No. 07/514,397, entitled "Treatment of Erectile Dysfunction" (published internationally as WO91/16021), the disclosure of which is incorporated by reference herein, transurethral administration of vasodilator can be carried out in a number of different ways. For example, the drug can be introduced into the urethra from a flexible tube, squeeze bottle, pump or aerosol spray. The agent may also be contained in coatings, pellets or suppositories which are absorbed, melted or bioeroded in the urethra. In certain embodiments which are illustrated in FIGS. 1 and 3, the agent is included in a coating on the exterior surface of a penile insert.

Referring now to FIG. 1, a penile insert 1 comprises a shaft portion 2 which is sized to be easily and comfortably inserted into the male urethra. It is preferable, however, that the end of shaft 2 is provided with an enlarged terminal portion 3 configured to prevent complete insertion into the urethra and to facilitate removal of the device after the agent has been delivered. The internal end of shaft portion 2 is preferably provided with a rounded, blunted end to prevent discomfort on insertion and is typically from about 3 to 5 millimeters in diameter and from about 2 to 12 centimeters in length.

The insert itself may be made from any pharmacologically acceptable material and although it may be rigid, it is preferred that the device be relatively soft and flexible for purposes of comfort, merely having sufficient rigidity to facilitate insertion. For this purpose, various pharmaceutically acceptable natural or synthetic rubber or polymeric materials may be used, such as natural rubber, silicone rubber, ethylene vinyl acetate (EVA) copolymers, polyethylene, polypropylene, polycarbonate, polyester, polyurethane and polyisobutylene polymers.

Although the vasoactive agent and any carriers, enhancers, or the like may be dispersed throughout the body of the insert 1, it is preferable that the agent be concentrated on the urethra-contacting surfaces of the device in order to permit rapid absorption of the agent and any carrier, enhancer, or the like. As shown in FIG. 1, the shaft portion 2 of the insert 1 is provided with an agent-containing coating 4 which comprises the desired agent dose and, if used, a permeation enhancer, dispersed throughout a rapidly releasing carrier. The coating 4 may be applied to the insert by means of dip coating in an appropriate agent-containing bath, spray coating, heat melt coating, evaporation of a fixed volume of a solution or suspension of the agent in a volatile vehicle or by co-extrusion of an agent-containing layer onto the surface of shaft 2, for example.

To facilitate insertion, coating 4 preferably has lubricating properties and may contain materials such as polyethylene glycol ("PEG"), propylene glycol, or hydroxy alkyl celluloses, for example, which are or become slippery upon insertion into the urethra. Materials such as glycerol monolaurate, polyethylene glycol monolaurate, and glycerol monolaurate, for example, may combine permeation enhancing properties with lubricating properties.

To facilitate adherence of the drug coatings to the penile insert, the surfaces to which the coatings are applied may be slightly roughened. Also, to provide a visual indication of complete agent release, the coating, instead of being clear and transparent, can be selected to provide a different visual appearance from that of the uncoated insert. This can be accomplished with the use of dyes or pigments or can be a property of the agent or coating material itself.

In use, the device is to be inserted into the urethra up to the terminal portion 3 and either maintained in place until the agent is absorbed. With shorter devices (about 2–5 cm in length), the device 1 would be inserted into the urethra up to portion 3 and then, while compressing the penis around shaft 2, gently but firmly rotated and reciprocated to wipe all the agent-containing material from the surface of the device prior to removal.

When the agent dose is formed from a water-soluble material such as PEG, it is also preferable that the patient urinate shortly before administration of the dose. The residual urine in the urethra causes the dose to dissolve more rapidly producing more rapid drug absorption.

Figure 2:
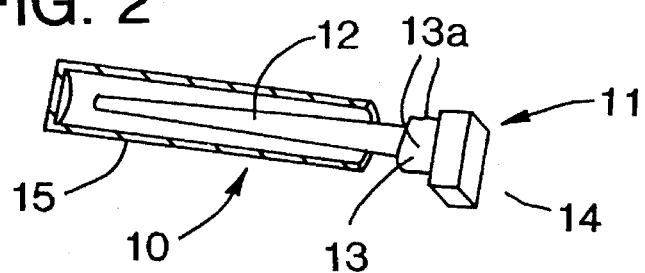
FIG. 2 is a cross-sectional view of a second embodiment of such a device.

Referring now to FIG. 2, a combination insert 10 is shown in which the insert 11 is provided with a tapered agent-carrying shaft portion 12 which terminates in a plug portion 13 which may also be provided with sealing ridges 13a. Plug element 13 terminates in cap portion 14 which may be larger than plug 13 and preferably of a square or other polygonal configuration to make it easy to rotate insert 11 for removal from its container 15. Container 15 is generally tubular in shape closed at one end and of sufficient length to receive the insert up to contact with cap 14. The interior diameter of container 15 and the exterior diameter of plug 13 with sealing ridges 13a are selected to provide a sliding seal that is sufficient to prevent insert 1 from falling out of the container and the passage of contaminants into the container while permitting removal of the insert with the application of a reasonable force on cap 14.

Referring now to FIG. 3, another embodiment of the invention is shown in which the penile insert 20 comprises a shaft portion 22 adapted to be receive within the male urethra and a terminal portion 23 in the form of a tubular cap adapted to enclose the glans and, if more agent delivering surface is required, some portion of the shaft of penis 17. The body-contacting surface of insert 20 is provided with an agent-containing coating 24 similar to that described with respect to FIG. 1 which coating is applied to the shaft 22 and such other portion of the interior of the terminal portion 23 as is desired. The embodiment of FIG. 3 may be used with respect to less potent agents which require an administration rate greater than can be obtained directly through the urethra. Thus, the portion of the coating 24 which contacts the glans and the shaft of the penis also provides for the administration of the agent directly through the skin of the penis in addition to the transurethral administration.

In use, the device would be inserted into the urethra 16 and in contact with the skin of penis 17 and maintained in place until all the agent has been released from coating 14.

In the practice of this invention it is desirable that the entire dose of drug be reproducibly deposited in contact with the urethra at the desired location within the urethra. Because the coatings on the inserts of FIGS. 1–3 are in contact with the urethra during the insertion and removal procedure, it is possible that some of the coating may be deposited at nonoptimum locations or that all of the coating may not be removed prior to withdrawal of the insert. In order to obtain a more precise control of the dose administered and the site of application, the dose can be contained within the insert where it is protected from contact with the urethra during insertion and means can be provided to positively displace the entire dose from the insert into the urethra at the desired depth of application.

Figure 4:
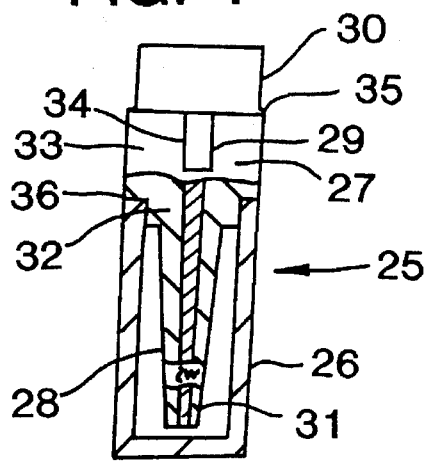
FIG. 4 is a side view, partly in section, of an inserter/container assembly for introducing a drug into the urethra.
Figure 5:
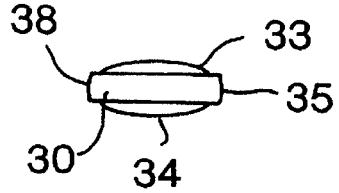
FIG. 5 is a top view of the inserter/container of FIG. 4.

Referring now to FIGS. 4 and 5, another embodiment of this invention is shown for use when the agent is contained in an ointment, paste, suppository, cream or gel formulation of the type described above rather than as a coating on the shaft of an inserter. The dosage inserter/container 25 comprises a container 26 closed at one end and receiving inserter 27 in the other end. Although container 26 can be cylindrical in configuration, it is preferred to form container 26 into a more volume efficient flattened configuration such as elliptical or rectangular because there is no need to maintain a large clearance between the exterior of inserter 27 and the interior of container 26, to prevent inadvertent removal of any coating on inserter 27. Inserter 27 comprises a shaft portion 28 having an external configuration similar to that of the inserter shown in FIGS. 1 and 2 but provided with a longitudinal bore which receives the piston portion 29 of plunger 30, the agent-containing dose 31 in the form of an ointment, paste, suppository, cream or gel having sufficient viscosity to enable it to remain, without spillage, within the cavity formed between the tip of piston 29 and the end of the bore. The bore may communicate with the urethra through the single outlet shown in FIG. 4 through which the dose is ejected by movement of piston 29. Alternatively, the end of the inserter could be provided with a multiplicity of small holes distributed about the tip through which the dose could be extruded in small streams into contact with the urethra.

Preferably, means are provided to prevent unintentional activation of plunger 30 which in its simplest form could be a frangible bead or bond which resists relative motion of plunger 30 with respect to shaft portion 28 until a predetermined force is applied. A more positive means is illustrated in FIGS. 4 and 5 wherein shaft portion 28 terminates in a plug portion 32 configured to form a sliding seal with the interior of container 26. The plug portion 32 terminates in cap portion 33 provided with receptacle means 34 configures to receive plunger 30 when plunger 30 is in a first position and to be incapable of receiving plunger 30 when in a second position and being of sufficient depth to allow displacement of piston 29 over sufficient travel to fully displace dose 31 from the inserter. In FIGS. 4 and 5 the receptacle 34 is shown as a slot across cap 33, Plunger 30 is mounted transverse to slot 34 and maintained in this first position by a frangible bond 35. Cap 33 is likewise sealed to container 26 by a similar frangible bond 36. These frangible bonds can be formed by any suitable technique which include adhesive bonding, heat or sonic welding or the application of some form of "shrink wrap" material, for example.

This configuration is readily adaptable to automated filling together with precise control of the quantity of dose 31 and provides for positive administration of the desired quantity of agent at the desired site of application.

Prior to use the device is protected from inadvertent displacement of dose 31 by means of the frangible seal 35 and inadvertent removal of the inserter by means of frangible seal 36. In use, frangible seal 35 would be broken by rotating plunger 30 from its first position to a second position where it is in alignment with receptacle 34 and frangible seal 36 would be broken to remove the inserter 27 from container 26. The inserter would then be placed into the urethra to the depth of plug 32 and plunger 30 depressed into receptacle 34 to completely eject dose 31 into the urethra at the desired point of application. The inserter 27 would then be removed leaving the dose 31 within the urethra.

The materials used to form the inserter/container 25 are the same as those which can be used in fabricating the devices of FIGS. 1 and 2 for example and when these materials are thermoplastic the formation of the frangible bonds 35 and 36 by sonic fusion is a preferred technique.

In order to assure the complete displacement of dose 31 by piston 29, relatively precise tolerances must be maintained with respect to the internal and external diameters of the bore through shaft portion 28 and of the piston 29, respectively. FIGS. 6, 7 and 8 describe a device in which manufacturing tolerances can be more relaxed while still maintaining positive displacement of the entire dose to the urethra at the desired position. Inserter 40 of FIGS. 6, 7 and 8 comprises a sleeve 41 which is preferably slightly thinner or otherwise weakened about the periphery of its distal end 42 such that this portion is more flexible than the remainder of sleeve 41 so that it will deform preferentially at this location. Sleeve 41 is also preferably provided with a thickened terminal portion 43. Sleeve 41 is sized to be received within the male urethra and preferably terminates at a shoulder 44 on handle 45, shoulder 44 being of sufficient diameter to prevent insertion into the urethra. Sleeve 41 may be formed as a unit with handle 45 or it may be formed separately and bonded or otherwise attached to shoulder 44. Handle 45 is provided with a central bore having a diameter corresponding to the interior of sleeve 41 and piston 46 is slidably received within sleeve 41 and handle 45. The distal end of piston 46 is firmly connected to the interior portion of the end portion 43 of sleeve 41. When piston 46 is moved to a position where it completely fills sleeve 42, the inserter has the configuration shown in FIG. 6. However, when piston 46 is withdrawn slightly from the position of FIG. 6, the end 43 of sleeve 41 will be withdrawn with the piston to form a cup-shaped cavity into which a suppository 47, preferably spherical, comprising the agent dose can be received. Upon further withdrawal to the position shown in FIG. 8, the peripheral portion 42 of the end of the sleeve 41 will have been withdrawn by piston 46 into the sleeve 41 causing it to surround and envelop suppository 47.

In operation, the spherical suppositories 47 are fabricated in the frozen condition by any of the conventional techniques used for the manufacture of spherical granules of predetermined size. Equipment for manufacturing small spherical particles is known to the art and includes rotary processing, multiple-step extrusion and spheronization equipment. Suitable equipment is available, for example, from Niro-Aeromatic, Inc. of Columbia, Md.

To load the inserter, piston 46 is moved to the position shown in FIG. 7 and the frozen suppository 47 deposited in the cup shaped receptacle so formed. The piston 46 would then be withdrawn to the position shown in FIG. 8 completely enclosing and enveloping the suppository 47 within the retroverted tip 42 of the sleeve. In use, the loaded inserter would be inserted into the male urethra until shoulder 44 abuts the meatus and plunger 46 moved forward to the position shown in FIG. 6 thereby releasing suppository 47 from the tip of the inserter and depositing at the desired depth.

Inserter 40 may be made from any of the materials described in connection with the embodiments of FIGS. 1–4 and may be provided with means for preventing inadvertent actuation as described with respect to FIGS. 4 and 5. For example, after the inserter is loaded with the suppository as shown in FIG. 8, sonic bonds could be formed between the handle 45 and the piston 46 or a cap-like structure similar to that of FIGS. 4 and 5 could be employed.

Figure 9:
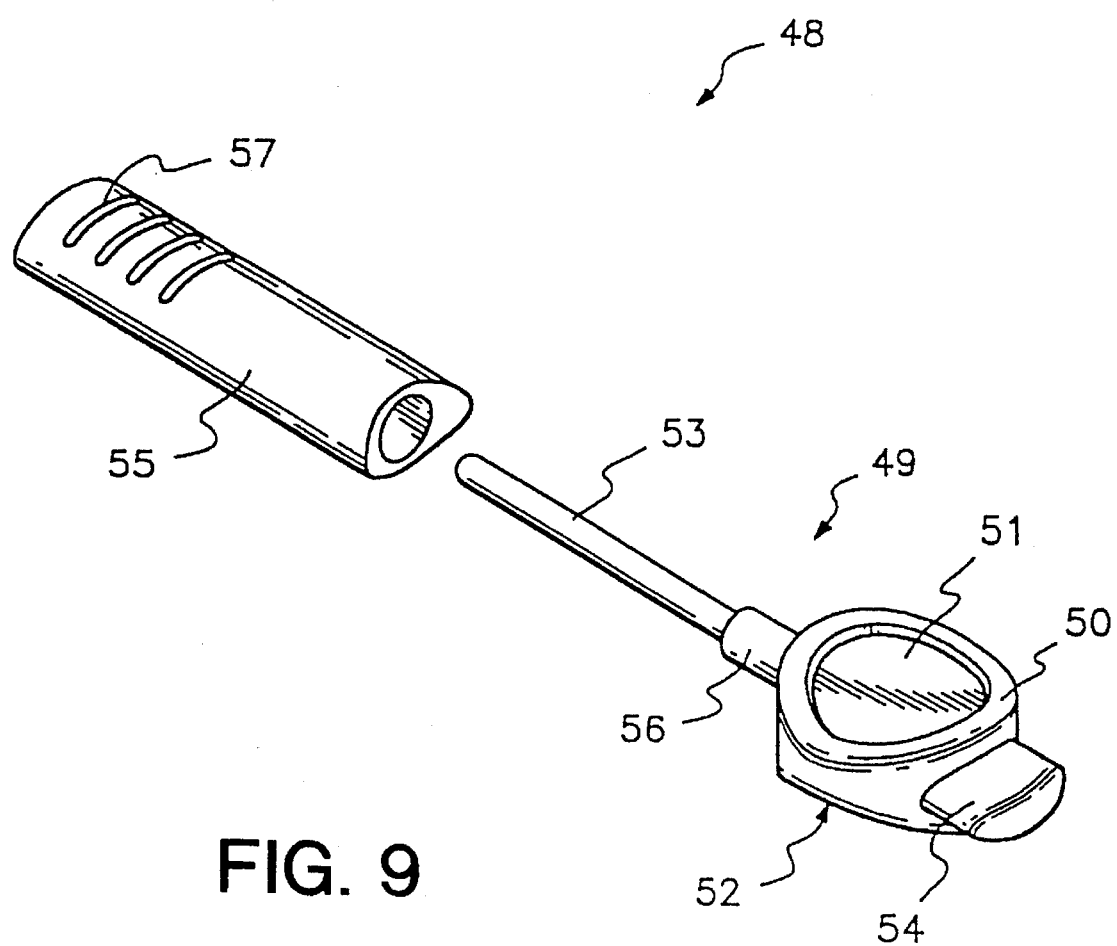
FIG. 9 is an exploded view of a further embodiment of a device which may be used in conjunction with the present method.

FIG. 9 illustrates another embodiment of the invention, wherein a transurethral drug delivery device is shown generally at 48. The device comprises a transurethral inserter 49 having an easily graspable segment 50 that has opposing symmetrically concave surfaces 51 and 52 adapted to be held by two fingers. Drug is contained within shaft 53, which is sized to fit within the urethra. A longitudinal plunger, the tip of which is seen at 54, is slidably insertable into the longitudinal bore contained within shaft 53. To extrude drug into the urethra, shaft 53 is inserted into the urethra, and plunger tip 54 is pushed into segment 50. The inserter 49 is then removed. Prior to use, and during storage, the device is capped with elongate cap 55 which fits snugly over flange 56 at the proximal end of shaft 53. The cap 55 is provided with a series of parallel ridges 57 to facilitate gripping of the cap and removal from inserter 49.

Although in the configurations shown in FIGS. 4–9 are preferred configurations, other inserter/container configurations can be used and any mechanism by which a predetermined quantity of drug can be introduced from the inserter at a predetermined depth in the urethra is suitable for use with this invention. The aforementioned devices can either be manufactured under sterile conditions, thereby eliminating the need for post-manufacturing sterilization, or they can be manufactured under non-sterile conditions and then subsequently sterilized by any suitable technique, e.g., radiation sterilization. The devices can be manufactured by typical plastic forming and coating processes known in the art, including molding extrusion, heat forming, dip coating, and the like.

After administration of the vasodilator, various penile hemodynamic parameters are measured, typically including cavernosal artery peak systolic velocity, cavernosal artery end diastolic velocities, maximum arterial dilation, and pressure. Based on these measurements, a determination is made as to whether penile vascular insufficiency is present.

It will be appreciated by those skilled in the art that any number of devices can be used to conduct the aforementioned measurements, providing that the desired level of accuracy is achieved. Duplex ultrasonography is the preferred mode of evaluating the penile hemodynamic parameters of interest. However, other types of techniques and equipment may be used as well, e.g., NMR spectroscopy, pressure cuffs, corpus cavernosograms, angiography, NPT (nocturnal penile tumescence) "Rigiscans," magnetic resonance imaging (MRI), computer aided tomography (CAT), pulsoximeters, and the like.

Examples of duplex ultrasonography devices which can be used in conjunction with the present method include those described in U.S. Pat. Nos. 4,334,543 to Fehr, 4,485,821 to Iinuma, and 4,612,937 to Miller, the disclosures of which are incorporated by reference herein. Suitable devices are available from a number of manufacturers, including, for example, Advanced Technology Laboratories (Bothell, Wash.) and Siemens Quantum (Issaquah, Wash.). In general, an apparatus is used which includes a transducing means for emitting ultrasound pulses, a means for receiving ultrasound reflected from the blood, and a detector circuit for determining the frequency difference between the transmitted and received ultrasound. The velocity of blood is then determined from the frequency difference. As explained in U.S. Pat. No. 4,612,937, individual velocity estimator signals are produced at a predetermined one of a plurality of points along each beam direction; these estimator signals are then coupled to a display, preferably a color display in which the brightness of color is proportional to the magnitude of blood flow velocity.

Based on the hemodynamic parameters measured using the aforementioned ultrasonography technique, a diagnosis can be made as to penile vascular sufficiency. Generally, if the measured PSV is less than about 50 cm/sec, more typically less than about 35 cm/sec, vascular inflow is insufficient, and a diagnosis of arterial insufficiency may be made. Alternatively, or additionally, if the measured EDV is greater than 0 cm/sec, more typically greater than about 5 cm/sec, a diagnosis of venous leakage may be made. In either case, the cause of erectile dysfunction is presumed to be vasculogenic, and the patient is then treated accordingly. A preferred mode of treating vasculogenic impotence involves the therapeutic regimen described in co-pending patent application Ser. No. 07/514,397, incorporated by reference above. Briefly, that mode of treatment comprises transurethrally administering a therapeutic composition containing a unit dosage of a vasodilating agent (suitable vasodilators are as identified earlier herein) and a dispersant which is selected so as to dissolve, melt or bioerode within the urethra to release the drug. Administration is repeated, incrementally increasing dosage if necessary, until the desired results are obtained.

If the diagnosis is that the patient's erectile dysfunction is due to other than vasculogenic causes, treatment will proceed accordingly depending on the factors involved, e.g., psychogenic, neurogenic, or the like.

The invention also encompasses a kit for conducting the diagnostic method. The kit contains the drug to be administered, a device for administering the drug transurethrally (e.g., as shown in the Figures herein), a sealed container housing the drug and device prior to use, and written instructions for carrying out the diagnostic method. The kit may include a means for administering the drug at different doses, or it may include different drugs, or a combination thereof. (That is, if the drug initially administered is not effective in inducing an erection, incrementally higher doses of drug can be used, or different drugs may be administered, until an erection is induced which is sufficient to enable measurement of the desired penile hemodynamic parameters.) Instruments for conducting the evaluation of one or more penile hemodynamic parameters may be included in the kit as well, e.g., a pressure cuff or the like.

As exemplified below, the method of the invention is as effective in providing diagnoses of vasculogenic erectile dysfunction as known methods which involve injection of the vasodilator. However, in contrast to these known methods, the present invention enables use of a noninvasive technique which avoids the pain of injection and the subsequent discomfort, and which involves easily used, inexpensive equipment.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Ten patients (20–57 yrs) with vasculogenic (8) or psychogenic (2) impotence underwent color-flow duplex ultrasound evaluation employing intracorporeal injection ("ICI") of prostaglandin $E_1$ (alprostadil, obtained from Upjohn; 10 μg), and Doppler Model No. ATL UM-9 (Advanced Technology Laboratories, Bothell, Wash.). Within 60 days, duplex ultrasound was repeated employing intraurethral administration of alprostadil using the drug administration device of FIG. 9. Patients, after voiding, administered the medication by inserting a 3 cm× 4 mm applicator that contains 500 μg Alprostadil, into the urethra. Erection occurred within minutes after application. Hemodynamic parameters examined at baseline, 5 and 15 minutes included: 1) cavernosal artery peak systolic velocity ("PSV") at baseline, 2) cavernosal artery end diastolic velocity ("EDV"), and 3) maximum arterial dilation.

The overall mean PSV following ICI was at 5 min: 35.4+/−13.8 cm/s (R) and 36.2+/−19.7 cm/s (L); at 15 min: 36.3+/−16.3 (R) and 37.1+/−17.8 cms (L). The overall mean PSV following intraurethral administration was at 5 min: 37.0+/−14.4 cm/s (R) and 29.5+/−19.7 cm/s (L); at 15 min 32.8+/−13.8 cms/(R) and 35.8+/−21.0 cm/s (L). There was no statistically significant difference between the responses to the two different modes of delivery on either cavernosal artery (t-test). In addition, within each individual the right and left cavernosal arterial response to ICI and intraurethral administration did not statistically differ at either 5 or 15 minutes (t-test). The EDV responses were identical. The maximum arterial dilation following ICI was 0.080+/−0.026 cm (R) and 0.078+/−0.012 cm (L). The maximum arterial dilation following MUSE was 0.078+/−0.030 cm (R) and 0.072+/−0.027 cm (L). The dilation response did not differ significantly (t-test). Additionally, the dilation responses to ICI versus intraurethral administration did not differ significantly within each individual (t-test). The most dramatic difference with intraurethral administration was observed in the cross-sectional demonstration of a diffuse arterial dilation in the extracorporal and periospongiosal arteries that often formed the origin for collateral intracorporal arterial inflow. Results are summarized in Table 1 and illustrated in graph form in FIGS. 10 through 13 (wherein the shaded bar represents the results obtained after injection of alprostadil while the unshaded bar represents the results obtained after intraurethral administration of alprostadil).

It may be concluded that transurethral administration effectively produced intracorporal smooth muscle relaxation comparable to intracavernosal injection of alprostadil (10 μg). This is demonstrated by arterial and veno-occlusive hemodynamic measurements of arterial dilation, arterial PSV increases, and EDV decreases (veno-occlusion). Furthermore, arterial dilation following transurethral administration appeared to be more diffuse compared to ICI.

This noninvasive method of delivering a vasodilating agent such as alprostadil can accordingly provide an equally effective and far more acceptable alternative to intracavernosal injection for patients undergoing duplex ultrasound evaluation for the diagnosis of erectile dysfunction.

TABLE 1

| n = 10 patients | Baseline | | 5 min | | 15 min | |
| --- | --- | --- | --- | --- | --- | --- |
| | inj | MUSE* | inj | MUSE | inj | MUSE |
| Mean Max. arterial diameter | | | | | | |
| Right | na | na | na | na | 0.08 | 0.08 |
| Left | na | na | na | na | 0.08 | 0.07 |
| Mean Peak Flow Velocity | | | | | | |
| Right | 7.40 | 5.91 | 35.44 | 37.02 | 36.28 | 32.83 |
| Left | 6.90 | 7.03 | 36.23 | 29.52 | 37.15 | 35.77 |
| Mean End Diastolic Velocity | | | | | | |
| Right | 0.00 | 0.00 | 7.14 | 10.91 | 5.24 | 7.87 |
| Left | 0.20 | 0.62 | 5.16 | 8.61 | 5.22 | 10.01 |

*MUSE: Medicated Urethral System for Injection, as illustrated in FIG. 9.

EXAMPLE 2

The procedure of Example 1 is repeated, except that $PGE_2$ is substituted for alprostadil. Substantially the same result will be obtained, i.e., that the diagnostic method involving transurethral administration of $PGE_2$ followed by hemodynamic evaluation will be at least as effective as the diagnostic method which involves intracavernosal injection of $PGE_2$, without the associated pain and discomfort. Hemodynamic evaluation may be conducted as in Example 1, using duplex ultrasonography, or it may be carried out using other techniques, e.g., NMR, angiography, or the like.

EXAMPLE 3

The procedure of Example 1 is repeated, except that phentolamine is substituted for alprostadil. Substantially the same result will be obtained, i.e., that the diagnostic method involving transurethral administration of phentolamine followed by hemodynamic evaluation will be at least as effective as the diagnostic method which involves intracavernosal injection of phentolamine, without the associated pain and discomfort. Hemodynamic evaluation may be conducted as in Example 1, using duplex ultrasonography, or it may be carried out using other techniques, e.g., NMR, angiography, or the like.

EXAMPLE 4

The procedure of Example 1 is repeated, except that a combination of $PGE_1$ and prazosin is substituted for alprostadil. Substantially the same result will be obtained, i.e., the diagnostic method involving transurethral administration of $PGE_1$ and prazosin followed by hemodynamic evaluation will be at least as effective as the diagnostic method involving intracavernosal injection of $PGE_1$ and prazosin, without the associated pain and discomfort. Hemodynamic evaluation may be conducted as in Example 1, using duplex ultrasonography, or it may be carried out using other techniques, e.g., NMR, angiography, or the like.

EXAMPLE 5

The procedure of Example 1 is repeated, except that a combination of $PGE_2$ and prazosin is substituted for alprostadil. Substantially the same result will be obtained, i.e., the diagnostic method involving transurethral administration of $PGE_2$ and prazosin followed by hemodynamic evaluation will be at least as effective as the diagnostic method which involves intracavernosal injection of $PGE_2$ and prazosin, without the associated pain and discomfort. Hemodynamic evaluation may be conducted as in Example 1, using duplex ultrasonography, or it may be carried out using other techniques, e.g., NMR, angiography, or the like.

EXAMPLE 6

The procedure of Example 1 is repeated, except that the device of FIG. 9 is replaced with a simple shaft coated with alprostadil (10 μg). Substantially the same result will be obtained, i.e., the diagnostic method involving transurethral administration of drug followed by hemodynamic evaluation will be at least as effective as the diagnostic method which involves intracavernosal injection, without the associated pain and discomfort. Hemodynamic evaluation may be conducted as in Example 1, using duplex ultrasonography, or it may be carried out using other techniques, e.g., NMR, angiography, or the like.

EXAMPLE 7

The procedure of Example 1 is repeated, except that the device of FIG. 9 is replaced with a pellet comprising a polyethylene glycol/alprostadil melt. Substantially the same result will be obtained, i.e., the diagnostic method involving transurethral administration of drug followed by hemodynamic evaluation will be at least as effective as the diagnostic method which involves intracavernosal injection, without the associated pain and discomfort. Hemodynamic evaluation may be conducted as in Example 1, using duplex ultrasonography, or it may be carried out using other techniques, e.g., NMR, angiography, or the like.

I claim:

1. A method for diagnosing erectile dysfunction in a male individual, comprising: (a) transurethrally administering to the individual a vasodilating agent in an amount sufficient to induce erection of the penis; (b) after erection has been induced, conducting penile hemodynamic measurements, wherein the hemodynamic measurements include evaluation of cavernosal artery peak systolic velocity, evaluation of cavernosal artery end diastolic velocity, or both; and (c) determining from the results in step (b) whether penile vascular insufficiency exists, such that it may be concluded that the erectile dysfunction is or is not a result of vasculogenic factors.

2. The method of claim 1, wherein the erectile dysfunction is impotence.

3. The method of claim 1, wherein the vasculogenic erectile dysfunction is Peyronie's syndrome.

4. The method of claim 1, wherein step (a) is carried out by placing the vasodilating agent in contact with the male urethra at a location between the proximal portion of the fossa navicularis and the distal portion of the pendulous urethra, such that the agent enters the individual's blood stream through the urethral wall.

5. The method of claim 4, wherein the agent is administered in a dispersant which releases the agent in the urethra at said depth at a weight ratio of dispersant to agent of about 1:1 to 10:1, wherein the dose of agent is selected so as not to exceed the dose retaining capacity of the urethra.

6. The method of claim 5, wherein approximately 50 mg of agent and dispersant are administered transurethrally.

7. The method of claim 1, wherein a transurethral permeation enhancer is administered with the vasodilating agent.

8. The method of claim 7, wherein the transurethral permeation enhancer and vasodilating agent are administered simultaneously.

9. The method of claim 8, wherein the transurethral permeation enhancer and vasodilating agent are administered in a single pharmaceutical composition.

10. The method of claim 7, wherein the transurethral permeation enhancer and vasodilating agent are administered sequentially.

11. The method of claim 1, wherein the vasodilating agent is selected from the group consisting of nitrates, long- and short-acting α-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and mixtures thereof.

12. The method of claim 1, wherein step (b) is conducted using ultrasonography.

13. The method of claim 12, wherein the ultrasonography is duplex ultrasonography.

14. The method of claim 13, wherein step (b) is conducted by transmitting ultrasound to each cavernosal artery, detecting ultrasound reflected therefrom, detecting the frequency difference between the transmitted and reflected ultrasound, and calculating the velocity of blood from the frequency difference.

15. The method of claim 1, wherein step (b) is conducted using angiography.

16. The method of claim 1, wherein step (b) is conducted using a corpus cavernosagram.

17. The method of claim 1, wherein the hemodynamic measurements include evaluation of maximum arterial dilation.

18. A method for treating erectile dysfunction in a male individual, comprising:
 (a) determining whether or not the erectile dysfunction is due to vasculogenic causes, comprising (i) transurethrally administering to the individual a vasodilating agent in an amount sufficient to induce erection of the penis, (ii) after erection has been induced, conducting penile hemodynamic measurements, wherein the hemodynamic measurements include evaluation of cavernosal artery peak systolic velocity, evaluation of cavernosal artery end diastolic velocity, or both, (iii) determining from the results in step (ii) whether penile vascular insufficiency exists, thereby making a diagnosis as to whether the erectile dysfunction is vasculogenic;
 (b) if the diagnosis in step (a) is that the erectile dysfunction is vasculogenic, transurethrally administering a vasodilating agent to the patient within the context of a treatment regimen which is effective to remedy the erectile dysfunction.

19. The method of claim 18, wherein step (b) is carried out by placing the vasodilating agent in contact with the male urethra at a location between the proximal portion of the fossa navicularis and the distal portion of the pendulous urethra, such that the agent enters the individual's blood stream through the urethral wall.

20. The method of claim 19, wherein the agent is administered in a dispersant which releases the agent in the urethra at said depth at a weight ratio of dispersant to agent of about 1:1 to 10:1, wherein the dose of agent is selected so as not to exceed the dose retaining capacity of the urethra.

21. The method of claim 18, wherein step (a)(ii) is conducted using ultrasonography.

22. The method of claim 21, wherein the ultrasonography is duplex ultrasonography.

23. The method of claim 22, wherein step (a)(ii) is conducted by transmitting ultrasound to each cavernosal artery, detecting ultrasound reflected therefrom, detecting the frequency difference between the transmitted and reflected ultrasound, and calculating the velocity of blood from the frequency difference.

24. The method of claim 18, wherein step (a)(ii) is conducted using angiography.

25. The method of claim 18, wherein the hemodynamic measurements include evaluation of maximum arterial dilation.

26. The method of claim 18, wherein the erectile dysfunction is impotence.

27. The method of claim 18, wherein the vasculogenic erectile dysfunction is Peyronie's syndrome.

28. The method of claim 18, wherein approximately 50 mg of agent and dispersant are administered transurethrally.

29. The method of claim 18, wherein a transurethral permeation enhancer is administered with the vasodilating agent.

30. The method of claim 29, wherein the transurethral permeation enhancer and vasodilating agent are administered simultaneously.

31. The method of claim 30, wherein the transurethral permeation enhancer and vasodilating agent are administered in a single pharmaceutical composition.

32. The method of claim 29, wherein the transurethral permeation enhancer and vasodilating agent are administered sequentially.

33. The method of claim 18, wherein the vasodilating agent is selected from the group consisting of nitrates, long- and short-acting α-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and mixtures thereof.

34. A method for diagnosing erectile dysfunction in a male individual, comprising: (a) transurethrally administering to the individual a vasodilating agent in an amount sufficient to induce erection of the penis; (b) after erection has been induced, conducting penile hemodynamic measurements using NMR spectroscopy; and (c) determining from the results in step (b) whether penile vascular insufficiency exists, such that it may be concluded that the erectile dysfunction is or is not a result of vasculogenic factors.

35. The method of claim 34, wherein the erectile dysfunction is impotence.

36. The method of claim 34, wherein the vasculogenic erectile dysfunction is Peyronie's syndrome.

37. The method of claim 34, wherein step (a) is carried out by placing the vasodilating agent in contact with the male urethra at a location between the proximal portion of the fossa navicularis and the distal portion of the pendulous urethra, such that the agent enters the individual's blood stream through the urethral wall.

38. The method of claim 37, wherein the agent is administered in a dispersant which releases the agent in the urethra at said depth at a weight ratio of dispersant to agent of about 1:1 to 10:1, wherein the dose of agent is selected so as not to exceed the dose retaining capacity of the urethra.

39. The method of claim 38, wherein approximately 50 mg of agent and dispersant are administered transurethrally.

40. The method of claim 34, wherein a transurethral permeation enhancer is administered with the vasodilating agent.

41. The method of claim 40, wherein the transurethral permeation enhancer and vasodilating agent are administered simultaneously.

42. The method of claim 41, wherein the transurethral permeation enhancer and vasodilating agent are administered in a single pharmaceutical composition.

43. The method of claim 40, wherein the transurethral permeation enhancer and vasodilating agent are administered sequentially.

44. The method of claim 40, wherein the vasodilating agent is selected from the group consisting of nitrates, long- and short-acting α-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and mixtures thereof.

45. The method of claim 34, wherein the vasodilating agent is selected from the group consisting of nitrates, long- and short-acting α-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and mixtures thereof.

46. A method for treating erectile dysfunction in a male individual, comprising:
(a) determining whether or not the erectile dysfunction is due to vasculogenic causes, comprising (i) transurethrally administering to the individual a vasodilating agent in an amount sufficient to induce erection of the penis, (ii) after erection has been induced, conducting penile hemodynamic measurements using NMR spectroscopy, (iii) determining from the results in step (ii) whether penile vascular insufficiency exists, thereby making a diagnosis of the erectile dysfunction is vasculogenic;
(b) if the diagnosis in step (a) is that the erectile dysfunction is vasculogenic, transurethrally administering a vasodilating agent to the patient within the context of a treatment regimen which is effective to remedy the erectile dysfunction.

47. The method of claim 46, wherein the erectile dysfunction is impotence.

48. The method of claim 46, wherein the vasculogenic erectile dysfunction is Peyronie's syndrome.

49. The method of claim 46, wherein step (a) is carried out by placing the vasodilating agent in contact with the male urethra at a location between the proximal portion of the fossa navicularis and the distal portion of the pendulous urethra, such that the agent enters the individual's blood stream through the urethral wall.

50. The method of claim 49, wherein the agent is administered in a dispersant which releases the agent in the urethra at said depth at a weight ratio of dispersant to agent of about 1:1 to 10:1, the amount of said dose not exceeding the dose retaining capacity of the urethra.

51. The method of claim 50, wherein the amount of agent and dispersant that is administered transurethrally is approximately 50 mg.

* * * * *